(12) United States Patent
Roso et al.

(10) Patent No.: US 7,431,938 B2
(45) Date of Patent: Oct. 7, 2008

(54) TEXTURIZING COMPOSITION FOR COSMETICS OR PHARMACEUTICALS

(75) Inventors: Alicia Roso, Saix (FR); Nelly Michel, Maisons Alfort (FR); Catherine Bulcourt, Boulogne Billancourt (FR)

(73) Assignee: Societe d'Exploitation de Produits pour les Industries Chimiques Seppic, Paris (FR)

( * ) Notice: Subject to any disclaimer, the term of this patent is extended or adjusted under 35 U.S.C. 154(b) by 519 days.

(21) Appl. No.: 10/774,268

(22) Filed: Feb. 6, 2004

(65) Prior Publication Data

US 2004/0191283 A1 Sep. 30, 2004

(30) Foreign Application Priority Data

Feb. 6, 2003 (FR) .................................. 03 01395

(51) Int. Cl.
*A61K 8/00* (2006.01)
*A61K 9/14* (2006.01)

(52) U.S. Cl. ........................ 424/401; 424/489
(58) Field of Classification Search .............. 424/401, 424/489; 514/937
See application file for complete search history.

(56) References Cited

U.S. PATENT DOCUMENTS

| 6,136,305 | A | 10/2000 | Michel-Lecocu et al. |
| 6,197,287 | B1* | 3/2001 | Mallo et al. ............ 424/70.16 |
| 6,268,400 | B1 | 7/2001 | Amalric et al. |
| 6,274,151 | B1 | 8/2001 | Michel et al. |
| 6,296,859 | B1 | 10/2001 | Stoltz |
| 6,346,239 | B1 | 2/2002 | Mallo et al. |
| 6,375,959 | B1 | 4/2002 | Mallo et al. |
| 6,673,861 | B2* | 1/2004 | Tabacchi et al. ............ 524/458 |
| 7,033,600 | B1* | 4/2006 | Mallo et al. .................. 424/401 |
| 2001/0002257 | A1 | 5/2001 | Stolz |
| 2001/0051686 | A1 | 12/2001 | Tabacchi et al. |
| 2001/0053801 | A1 | 12/2001 | Tabacchi et al. |
| 2002/0032243 | A1* | 3/2002 | Tabacchi et al. .............. 516/98 |
| 2003/0235547 | A1* | 12/2003 | Braun et al. ............. 424/70.11 |

FOREIGN PATENT DOCUMENTS

| EP | 0 995 487 A1 | 10/1999 |
| EP | 1 055 707 A | 11/2000 |
| FR | 2 721 511 | 6/1994 |
| FR | 2 773 805 | 1/1998 |
| FR | 2 774 688 | 2/1998 |
| FR | 2 774 996 | 2/1998 |
| FR | 2 782 086 | 8/1998 |
| FR | 2 785 801 | 11/1998 |
| FR | 2 786 493 | 11/1998 |
| FR | 2 787 457 | 12/1998 |
| FR | 2 789 395 | 2/1999 |

(Continued)

OTHER PUBLICATIONS

French Search Report for FR 0301395.

*Primary Examiner*—Johann Richter
*Assistant Examiner*—Konata M. George
(74) *Attorney, Agent, or Firm*—Young & Thompson (57) ABSTRACT

A texturizing composition and method utilized for foundations, makeup powders, mascaras, lipsticks, emulsions, lotions, gels, sprayable formulations, and solutions impregnated on fabrics, paper, towelettes or complexion corrector papers comprising at least one self-invertible inverse latex, and powder.

21 Claims, 1 Drawing Sheet

| | FOREIGN PATENT DOCUMENTS | | | US | EP 0 503 853 | * | 9/1992 |
|----|----------|--------|----|------------------|--|--------|
| | | | WO | WO 99 00109 | | 1/1999 |
| FR | 2 794 034 | 5/1999 | WO | WO 99 36445 | | 1/1999 |
| FR | 2 794 124 | 5/1999 | WO | WO 99 45899 | | 3/1999 |
| FR | 2 808 446 | 5/2000 | WO | WO 00 32639 | | 6/2000 |
| FR | 2 808 447 | 5/2000 | WO | WO 01 35922 A | | 5/2001 |
| FR | 2 810 883 | 6/2000 | | | | |

* cited by examiner

Figure 1

TEXTURIZING COMPOSITION FOR COSMETICS OR PHARMACEUTICALS

This application claims the benefit of priority under 35 U.S.C. § 119 (a) and (b) 1 to French Application No. 0301395, filed Feb. 6, 2003, the entire contents of which are incorporated herein by reference.

BACKGROUND OF THE INVENTION

1. Field of the Invention

The invention relates to novel compositions in powder form and to their use as a texturizer in cosmetic, dermopharmaceutical and pharmaceutical applications and in the treatment of paper or textiles.

2. Related Art

Texturizers are frequently used in producing formulations intended for caring for or making up the skin or mucosae or else in application to substrates such as paper or textiles. Their principal function is to enhance the sensorial and Theological properties of the formulations in which they are incorporated or of the substrates to which they are applied. Examples of texturizers used in cosmetology include polymethyl methacrylate powders (Micropearl™), polyamide powders (Nylon™), silicone powders (DC9506™, Polytrap™), and modified starches (Dry Flo™). Some of these powders produce in the user a sensation of softness on spreading and a lasting powdery feel; others inhibit the greasy sensation felt on spreading and bring about a long-lasting matting effect.

Some amino acid derivatives, such as N-lauroyl-lysine, are sometimes added to makeup formulas in order to combine the effects of softness on application and staying power on the skin. This effect may also be obtained by treating the surface of the powders with various compounds, including amino acids.

In certain cases fibres are also added to the formulations, either natural fibres such as cellulose or cotton fibres or synthetic fibres such as polyethylene, Teflon or polyester fibres, in order to modify the Theological characteristics of the formulas or to enhance both the uniformity of their distribution on the surface to be coated and their staying power thereon.

Certain fillers, such as talc, mica, sericite or else composite fillers, are also used in order to modify the lubricating properties of the formulation and to facilitate flow or spreading on the substrate.

Other types of pigmentary fillers, such as titanium oxide, zinc oxide or iron oxides, may also be incorporated into these formulations in order to modify their transparency or colour on application while influencing their final texture.

These powders are, generally speaking, well suited to the manufacture of loose powder or compact powder formulations or of formulations with a continuous fatty phase, such as water-in-oil emulsions, water-in-silicone-oil emulsions, sticks and other compact formulas.

In contrast, they are often difficult to employ in media having a continuous aqueous phase, such as lotions, gels, cream gels or oil-in-water emulsions. In such cases it is necessary to carry out specific and expensive preliminary studies, for each powder and each type of formulation, in order to obtain both effective dispersion of the powder and satisfactory stability of the formulation.

The formulator is then often compelled to use either hydrophilic microporous microspheres of Micropearl™ type, in combination with stabilizers, or powders which have been surface-treated to enhance compatibility with the other ingredients of the formulation. In this latter case, however, the appropriate treatment is specific to the formulation selected and, moreover, does not relieve the formulator of the task of a stability study on the treated powder selected within the formulation. Finally, this last solution is not generally suitable for formulations of the type with a continuous aqueous phase, either in the absence or in the presence of a small proportion of fatty phase.

Consequently, in the context of its research into improving the texture of formulations, the applicant has sought to develop new texturizers in powder form which are multifunctional and are easy to employ, both in solid formulations of loose powder or compact powder type and in formulations with a continuous fatty phase or in formulations with a continuous aqueous phase, with or without a small proportion of fatty phase.

SUMMARY OF THE INVENTION

The invention provides a composition consisting essentially of a mixture containing:
- from 1% to 90% by weight of at least one self-invertible inverse latex;
- from 99% to 10% by weight of the mixture of at least one cosmetically or pharmaceutically acceptable powder.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

A self-invertible inverse latex denotes more particularly a composition comprising an oil phase, an aqueous phase, at least one water-in-oil (W/O) emulsifier, at least one oil-in-water (O/W) emulsifier, containing from 20% to 70% by weight and preferably from 25% to 50% by weight of a branched or crosslinked polyelectrolyte, characterized in that the said polyelectrolyte is alternatively a homopolymer based on a monomer possessing either a strong acid function which is partly or totally in salt form or a weak acid function which is partly or totally in salt form, or a copolymer based on at least one monomer possessing a strong acid function copolymerized either with at least one monomer possessing a weak acid function or with at least one neutral monomer, or a copolymer based on at least one monomer possessing a weak acid function copolymerized with at least one neutral monomer or with a monomer possessing a weak acid function.

The term "water-in-oil emulsifier" refers to surfactants having a sufficiently low HLB to give water-in-oil emulsions, such as surfactant polymers of the polyethylene glycol poly (hydroxystearic acid) block copolymer type which are sold under the name Hypermer™, such as sorbitan esters, for instance sorbitan mono-oleate sold by the applicant under the name Montane™ 80, sorbitan isostearate sold by the applicant under the name Montane™ 70, sorbitan oleate ethoxylated with 5 moles of ethylene oxide (5 EO) sold by the applicant under the name Montane™ 81, diethoxylated (2 EO) oleocetyl alcohol sold by the applicant under the name Simulsol™ OC 72 or sorbitan sesquioleate sold by the applicant under the name Montane™ 83.

The term "oil-in-water emulsifier" denotes surfactants having a sufficiently high HLB to give oil-in-water emulsions, such as ethoxylated sorbitan esters, for instance sorbitan oleate ethoxylated with 20 moles of ethylene oxide (20 EO), sold by the applicant under the name Montanox™ 80, castor oil ethoxylated with 40 moles of ethylene oxide (40 EO), sold by the applicant under the name Simulsol™ OL 50, sorbitan laurate ethoxylated with 20 moles of ethylene oxide (20 EO), sold by the applicant under the name Montanox™ 20, sorbitan trioleate ethoxylated with 25 moles, sold by the applicant under the name Montanox™ 85, lauryl alcohol ethoxylated with 7 moles of ethylene oxide (7 EO), sold by the applicant under the name Simulsol™ P 7, decaethoxylated (10 EO) oleocetyl alcohol, sold by the applicant under the name Simulsol™ OC 710 or polyethoxylated sorbitan hexa-oleates sold under the names G-1086™ and G-1096™.

A branched polymer is a non-linear polymer having pendant chains resulting, when this polymer is dissolved in water, in an advanced stage of entanglement, leading to very high viscosities at low shear rate.

A crosslinked polymer is a non-linear polymer in the form of a three-dimensional network which is insoluble in water but which can be swollen in water, so leading to the preparation of a chemical gel.

The strong acid function of the monomer containing it is in particular the sulphonic acid function or the phosphonic acid function, partly or totally in the salt form. The said monomer may be, for example, styrenesulphonic acid partly or totally in salt form or, preferably, 2-methyl-2-[(1-oxo-2-propenyl) amino]-1-propanesulphonic acid partly or totally in salt form, in particular in the form alternatively (i) of an alkali metal salt, such as the sodium salt or potassium salt, for example, (ii) of an ammonium salt, (iii) of the salt of an amino alcohol, such as the monoethanolamine salt, for example, or (iv) of the salt of an amino acid, such as the lysine salt, for example.

The weak acid function of the monomer containing it is, in particular, the carboxylic acid function, and the said monomer is preferably selected from acrylic acid, methacrylic acid, itaconic acid, maleic acid and 3-methyl-3-[(1-oxo-2-propenyl)amino]butanoic acid, the said acids being partly or totally in salt form, in particular in the form alternatively (i) of an alkali metal salt, such as the sodium salt or potassium salt, for example, (ii) of an ammonium salt, (iii) of the salt of an amino alcohol, such as the monoethanolamine salt, for example, or (iv) of the salt of an amino acid, such as the lysine salt, for example.

The neutral monomer is selected in particular from acrylamide, methacrylamide, dimethylacrylamide, 2-hydroxyethyl acrylate, 2,3-dihydroxypropyl acrylate, 2-hydroxyethyl methacrylate, 2,3-dihydroxypropyl methacrylate, diacetoneacrylamide and an ethoxylated derivative of each of these esters with a molecular weight of between 400 and 1 000.

The invention more particularly provides a composition as defined above, characterized in that the anionic polyelectrolyte is crosslinked and/or branched with a diethylenic or polyethylenic compound in the molar proportion, expressed relative to the monomers employed, of from 0.005% to 1%, and preferably from 0.01% to 0.5%, and more particularly from 0.01% to 0.25%, preferably the proportion for which the crosslinking agent and/or the branching agent is selected from ethylene glycol dimethacrylate, diallyloxyacetic acid or a salt thereof such as sodium diallyloxyacetate, ethylene glycol diacrylate, diallylurea, triallylamine, trimethylolpropane triacrylate and methylenebis(acrylamide) or a mixture of these compounds.

The self-invertible inverse latex employed in the present invention contains generally from 2.5% to 15% by weight and preferably from 4% to 9% by weight of emulsifiers, of which from 20% to 50%, in particular from 25% to 40%, of the total weight of the emulsifiers present are of the water-in-oil (W/O) type and from 80% to 50%, in particular from 75% to 60%, of the total weight of the emulsifiers are of the oil-in-water (O/W) type.

In the self-invertible inverse latex employed in the present invention, in general, the oil phase represents from 15% to 40% and preferably from 20% to 25% of its total weight.

This oil phase is generally composed alternatively of a commercial mineral oil containing saturated hydrocarbons such as paraffins, isoparaffins and cycloparaffins, having at room temperature a density of between 0.7 and 0.9 and a boiling point of more than 180° C., such as, for example, Isopar™ L, Isopar™ M, Exxsol™ D 100 S or Marcol™ 52, which are sold by Exxon Chemical, isohexadecane or isododecane, or a vegetable oil, or glycerol esters, such as Softenol™3108, Softenol™3178, Softenol™3100, Softenol™3107 and Softenol™3118, or fatty acid esters, or a synthetic oil, or a mixture of two or more of these oils.

In one preferred embodiment of the present invention the oil phase is composed of Marcol™ 52, squalane, hydrogenated polyisobutene, octyl palmitate, isostearyl isostearate, isododecane or isohexadecane; isohexadecane, which is identified in Chemical Abstracts by the registry number (RN) 93685-80-4, is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9). It is sold in France by Bayer. Marcol™ 52 is a commercial oil meeting the definition of Vaseline oils in the French Codex. It is a white mineral oil conforming to the regulations FDA 21 CFR 172.878 and CFR 178.3620 (a) and it is recorded in the U.S. Pharmacopoeia US XXIII (1995) and in the European Pharmacopoeia (1993). Softenol™3819 is a mixture of fatty acid triglycerides containing 6 to 10 carbon atoms. Softenol™3108 is a mixture of fatty acid triglycerides containing 8 to 10 carbon atoms. Softenol™3178 is a mixture of fatty acid triglycerides containing 8 to 18 carbon atoms. Softenol™3100 is a mixture of fatty acid triglycerides containing 12 to 18 carbon atoms. Softenol™3107 is a mixture of fatty acid triglycerides containing 7 carbon atoms. Softenol™3114 is a mixture of fatty acid triglycerides containing 14 carbon atoms. Softenol™3118 is a mixture of fatty acid triglycerides containing 18 carbon atoms.

The self-invertible inverse latices employed in the present invention contain generally between 20% and 50% of water. They may also include various additives such as complexing agents, transfer agents or chain terminators.

Self-invertible inverse latices of this kind are described in the French patent applications and French patents published under numbers 2721511, 2773805, 2774688, 2774996, 2782086, 2785801, 2786493, 2787457, 2789395, 2794034, 2794124, 2808446, 2808447 and 2810883.

The term "cosmetically or pharmaceutically acceptable powder" refers in particular to powders of synthetic or natural origin which are organic or inorganic, hydrophilic or hydrophobic, with a mean diameter of between approximately 0.01 μm and approximately 250 μm and preferably between 1 and 50 μm, micronized or not, of any form, in particular in a fibre form, a lamellar form or a spherical form, which may have undergone a surface treatment.

Examples include copolymers of acrylic and methacrylic acid or their esters, starches, silicates, calcium, magnesium and barium silicates, calcium phosphate, boron nitride, lauroyllysine, silicone resin powders, calcium carbonate or magnesium carbonate, titanium oxide or zinc oxide or cerium oxide, iron oxides and other organic or inorganic pigments, or mixtures of these powders.

Fibres include, for example, natural fibres such as cotton, cellulose or chitosan fibres, synthetic fibres such as polyamide fibres, for instance Nylon™ fibres, Rayon™ fibres, Viscose™ fibres, cellulose acetate fibres, poly-p-phenyleneterephthalamide fibres such as Kevlar™ fibres, polyethylene or polypropylene fibres, glass fibres, carbon fibres, Teflon™ fibres, polyester fibres, polyvinyl chloride fibres, polyvinyl alcohol fibres, polyacrylonitrile fibres, polyurethane fibres or polyethylene phthalate fibres.

Powders in lamellar form include for example talcs, micas, mica-titaniums and sericite.

Powders in spherical form include, for example, polymethyl methacrylates, often referred to in the literature by the term PMMA, and formed of microporous microspheres with a specific surface area greater than or equal to 0.5 m$^2$ per gram, such as those sold under the names Micropearl™ M305, Micropearl™ M100, Micropearl™ 201 and Micropearl™ M310; copolymers, including terpolymers, of methyl methacrylate with one or more monomers selected from butyl acrylate, 1-methylpropyl acrylate, 2-methylpropyl acrylate, 1,1-dimethylethyl acrylate, butyl methacrylate, 1-methylpropyl methacrylate, 2-methylpropyl methacrylate and 1,1-dimethylethyl methacrylate, such as those sold under the name Microsphere™;

silica microspheres such as those sold under the names Silica beads™ or Polytrap™;

hollow thermoplastic microspheres such as polyethylenes, polystyrenes, polyacrylonitriles, or polyamides, such as those sold under the name Orgasol™ or else hollow polyester microspheres such as those sold under the name Expancel™;

microcapsules made of organic or inorganic material, such as those sold under the name Macrolite™.

The invention more particularly provides a composition as defined above consisting essentially of a mixture containing:
  from 5% to 80% by weight of at least one self-invertible inverse latex and
  from 20 to 95% of a cosmetically or pharmaceutically acceptable powder.

In a first preferred embodiment of the present invention the self-invertible inverse latex present in the composition as defined above is selected from the self-invertible inverse latices of the following polyelectrolytes:
  copolymer of acrylic acid partly in sodium salt form and acrylamide, crosslinked with methylenebis-(acrylamide);
  copolymer of 2-methyl-2-[(1-oxo-2-propenyl)-amino]-1-propanesulphonic acid partly in sodium salt form and acrylamide, crosslinked with methylenebis-(acrylamide);
  copolymer of 2-methyl-2-[(1-oxo-2-propenyl)-amino]-1-propanesulphonic acid partly in sodium salt form and acrylic acid partly in sodium salt form, crosslinked with methylenebis(acrylamide);
  copolymer of 2-methyl-2-[(1-oxo-2-propenyl)-amino]-1-propanesulphonic acid partly in sodium salt form and 2-hydroxyethyl acrylate, crosslinked with methylenebis(acrylamide);
  homopolymer of 2-methyl-2-[(1-oxo-2-propenyl)-amino]-1-propanesulphonic acid partly in sodium salt form, crosslinked with methylenebis(acrylamide);
  homopolymer of acrylic acid partly in ammonium salt or monoethanolamine salt form, crosslinked with sodium diallyloxyacetate; or
  homopolymer of acrylic acid partly in ammonium or monoethanolamine salt form, crosslinked with triallylamine.

The self-invertible inverse latices defined above include the compositions sold under the brand names Sepigel™ 305 (INCI name: Polyacrylamide and C13-C14 Isoparaffin and Laureth-7), Sepigel™ 501 (INCI name: Acrylamides Copolymer and Mineral oil and Paraffin liquidum and C13-C14 Isoparaffin and Polysorbate 85), Sepigel™ 502 (INCI name: C13-C14 Isoparaffin and Isostearyl isostearate and Sodium polyacrylate and Polyacrylamide and Polysorbate 60), Simulgel™ EG (INCI name: Sodium acrylate and Acryloyldimethyl Taurate Copolymer and Isohexadecane and Polysorbate 80), Simulgel™ NS (INCI name: Hydroxyethyl Acrylate and Sosium Acryloyldimethyl Taurate Copolymer and Squalane and Polysorbate 60), Simulgel™ A (INCI name: Ammonium Polyacrylate and Isohexadecane and Polysorbate 89), Simulgel™ 600 (INCI name: Acrylamide and sodium Acryloyldimethyl Taurate Copolymer and Polysorbate 80), Simulgel™ 800 (INCI name: sodium Polyacryloyldimethyl Taurate and Isohexadecane and Sorbitan oleate), Simulgel™ HT (INCI name: Polyacrylamide and paraffin oil and Polysorbate 80), Simulgel EPG™ (INCI name: Sodium Acrylate and Acryloyldimethyl Taurate copolymer and Polyisobutene and Caprylyl capryl Glucoside).

In a second particular embodiment of the present invention it provides a composition as defined above in which the powder is selected from powders in spherical form, such as polymethyl methacrylates, for example, often referred to in the literature as PMMA, formed of microporous microspheres with a specific surface area greater than or equal to 0.5 m$^2$ per gram, such as those sold under the names Micropearl™ M305, Micropearl™ M100, Micropearl M310™; Micropearl MHB™; and Micropearl 201™; copolymers, including terpolymers, of methyl methacrylate with one or more monomers selected from butyl acrylate, 1-methylpropyl acrylate, 2-methylpropyl acrylate, 1,1-dimethylethyl acrylate, butyl methacrylate, 1-methylpropyl methacrylate, 2-methylpropyl methacrylate and 1,1-dimethylethyl methacrylate, such as those sold under the name Microsphere™ or Sepipress™ M.

In a third particular embodiment of the present invention the composition contains at least 50% by weight of powder as defined above.

In a fourth particular embodiment of the present invention the composition as defined above is in the form of a homogeneous powder.

The invention further provides a process for preparing the composition as defined above by simple mixing of the self-invertible inverse latex with the powder.

The compositions provided by the present invention are used as formulation texturizers in cosmetic or pharmaceutical formulations, both liquid and solid and can be combined with a lot of cosmetic or pharmaceutical excipients or active ingredients. Their physical and sensorial properties, relating either to their very gentle feel, improve relative to the powder used on its own, or their excellent adhesion to the skin, greater than that of the powder to be used alone, and their capacity for homogeneous suspension in the end formulations, make them particularly appropriate for use in solid formulations such as foundations, makeup powders, mascaras or lipsticks. Where they are employed in liquid formulations those formulations may in particular be emulsions, lotions or gels, and more particularly sprayable formulations or else solutions impregnated on fabrics or paper and more particularly on towelettes or on complexion corrector papers.

The examples which follow illustrate the invention without, however, limiting it.

A) Demonstration of the differences in behaviour between the compounds of the invention and conventional texturizers in powder form:

(1)—Suspension Properties—Stability of the Aqueous Dispersion

A composition (1) according to the invention was prepared by mixing, by stirring alone, Micropearl™ M310 and Simulgel™ EG in a 60/40 weight ratio and then its properties were compared with Micropearl™ M310 alone (control powder ($t_1$)) and with an equivalent formulation prepared by successive incorporation of Micropearl™ M310 and Simulgel™ EG (control ($t_2$)=state of the art).

This was done by preparing aqueous dispersions of the powder according to the invention and of the control powder ($t_1$) at 2% by weight in water by mechanical stirring with a deflocculating turbomixer.

The control preparation ($t_2$), containing the same proportion by weight of Micropearl™ M310 and Simulgel™ EG as composition (1), these ingredients having been added successively, is likewise prepared with the same mechanical stirring by means of a deflocculating turbomixer.

Figure 1A:
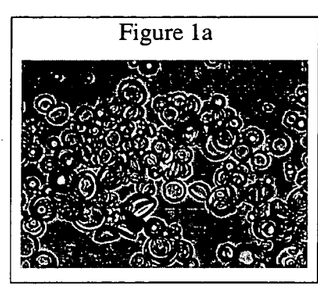
FIG. 1a illustrates the microscopic appearance (×400) of the control (t1), which is a white and heterogeneous particle agglomeration.
Figure 1B:
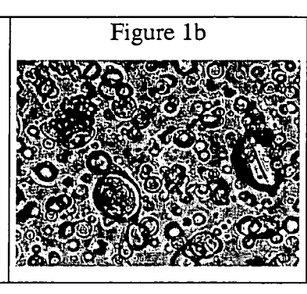
FIG. 1b illustrates the microscopic appearance (×400) of the control (t2), which is an opaque white and homogenous particle agglomeration.
Figure 1C:
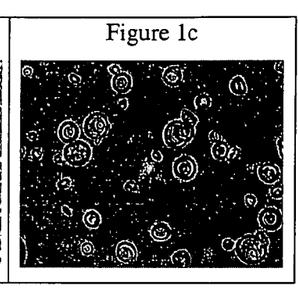
FIG. 1c illustrates the microscopic appearance (×400) of the composition (1), which is an opaque white and homogenous particle dispersion.

The observations and analyses of dispersions are noted in the following table:

|  | control ($t_1$) | control ($t_2$) | composition (1) |
|---|---|---|---|
| Visual appearance | white and heterogeneous | opaque white and homogeneous | opaque white and homogeneous |
| Microscopic appearance (× 400) | Particle agglomeration (see FIG. 1a) | Particle agglomeration (see FIG. 1b) | Effective of particle dispersion (see FIG. 1c) |
| Brookfield viscosity LVT (spindle: 2; speed: 6) | <50 mPa · s |  | 450 mPa · s |
| Stability at 25° C. | precipitates after 24 h |  | stable for 1 year |
| Stability at 40° C. | precipitates after 24 h |  | stable for more than 6 months |
| Stability at 50° C. | precipitates after 24 h |  | stable for more than a month |
| Feel | impossible to evaluate feel — product separates into phases | easy spreading; fresh and very gentle feel; residual powder effect | easy spreading; fresh and very gentle feel; residual powder effect |

(2)—A composition according to the invention was prepared by simply mixing Micropearl™ M310 and Simulgel™ EG in an 80/20 weight ratio, and then its properties were compared with a dispersion of Micropearl™ M310 alone (control $t_1$) and with the equivalent preparation in weight %, consisting of successive addition of Micropearl™ M310 and Simulgel™ EG (control preparation $t_3$=state of the art). This was done by preparing aqueous dispersions of the powder according to the invention (composition 2) and of the control powder (powder $t_1$) at different concentrations in water by mechanical stirring with a deflocculating turbomixer, and the equivalent preparations in weight % containing Micropearl™ M310 and Simulgel™ EG added successively (by an identical stirring method).

The results of the observation and analysis of the dispersions are recorded in the following table:

|  |  | Concentration in % w/w | | |
|---|---|---|---|---|
|  |  | 2% | 3% | 4% |
| Appearance | ($t_1$) | opaque white liquid | opaque white liquid | opaque white liquid |
|  | ($t_3$) | opaque white liquid | opaque white liquid | white milk |
|  | (2) | opaque white fluid | opaque white fluid | white milk |
| Microscopic appearance (× 400) | ($t_1$) | particle agglomerate | particle agglomerate | particle agglomerate |
|  | ($t_3$) | particle agglomerate | particle agglomerate | particle agglomerate |
|  | (2) | effective particle dispersion | effective particle dispersion | effective particle dispersion |
| Viscosity in mPa · s (Brookfield LVT spindle 2 speed 6) | ($t_1$) | <50 | <50 | <50 |
|  | ($t_3$) | 80 | 400 | 2 000 |
|  | (2) | 150 | 600 | 1 250 |
| Stability at 25° C. | ($t_1$) | 24 h | 24 h | 24 h |
|  | ($t_3$) | 24 h | 1 week | 3 months |
|  | (2) | 1 year | 1 year | 1 year |
| Stability at 40° C. | ($t_1$) | 24 h | 24 h | 24 h |
|  | ($t_3$) | 24 h | 1 week | 2 months |
|  | (2) | 6 months | 6 months | 6 months |
| Stability at 50° C. | ($t_1$) | 24 h | 24 h | 24 h |
|  | ($t_3$) | 24 h | 24 h | 1 month |
|  | (2) | >1 month | >1 month | >1 month |
| Feel | ($t_1$) | unstable | unstable | Unstable |
|  | ($t_3$) | very soft feel, residual | | fresh effect; easy spreading; very soft feel; remanent powdery feel |
|  | (2) | powder effect | | |

|  |  | Concentration in % w/w | | |
|---|---|---|---|---|
|  |  | 5% | 10% | 20% |
| Appearance | ($t_1$) | opaque white liquid | opaque white liquid | opaque white liquid |
|  | ($t_3$) | white milk | granular white gel | granular white gel |
|  | (2) | white milk | white gel | white gel |
| Microscopic appearance (× 400) | ($t_1$) | particle agglomerate | particle agglomerate | particle agglomerate |
|  | ($t_3$) | particle agglomerate | particle agglomerate | particle agglomerate |
|  | (2) | effective particle dispersion | effective particle dispersion | effective particle dispersion |
| Viscosity in mPa · s (Brookfield LVT spindle 2 speed 6) | ($t_1$) | <50 | <50 | <50 |
|  | ($t_3$) | 10 600 | 62 000 | >100 000 |
|  | (2) | 19 000 | 69 000 | >100 000 |
| Stability at 25° C. | ($t_1$) | 24 h | 24 h | 24 h |
|  | ($t_3$) | 1 year | 1 year | 1 year |
|  | (2) | 1 year | 1 year | 1 year |
| Stability at 40° C. | ($t_1$) | 24 h | 24 h | 24 h |
|  | ($t_3$) | 1 year | 1 year | 1 year |
|  | (2) | 6 months | 6 months | 6 months |
| Stability at 50° C. | ($t_1$) | 24 h | 24 h | 24 h |
|  | ($t_3$) | 1 year | 1 year | 1 year |
|  | (2) | >1 month | >1 month | >1 month |
| Feel | ($t_1$) | unstable | unstable | Unstable |
|  | $t_3$) | fresh effect; easy spreading; very soft | | |
|  | (2) | feel; remanent powdery feel | | |

The compositions according to the invention allow very simple formulation, with a single ingredient, of formulas having a notable feel, excellent stability on storage and a viscosity which can be modified ideally. The compositions according to the invention have the advantage of providing flawless dispersion of the powder, in contrast to formulations resulting from the successive introduction of Micropearl™ and Simulgel™, even at high levels of powder. The stability of the formulations is likewise significantly enhanced for the lower levels of powder.

These dispersions may be used advantageously for all types of makeup or care formulas in continuous aqueous phase alone, whether the initial powders are hydrophilic, such as Micropearl™ M305, or hydrophobic, such as Micropearl™ M310.

(3)—Stabilizing Effect within a Water-in-Silicone Emulsion

A series of emulsions in silicone oils were prepared on the basis of the following formula:

| Phase A | |
|---|---|
| DC5225C ™ | 20% by weight |
| DC345 ™ | 10% by weight |
| Sepicide ™ HB | 0.3% by weight |
| Powder (3) (Micropearl ™ M310 + Simulgel ™ EG, weight ratio 8/2) | x% by weight or |
| Control powder (t) (Micropearl ™ M310) | x% by weight |
| Phase B | |
| Water | qs 100% |
| Sepicide ™ CI | 0.2% by weight |
| Glycerin | 5% by weight |
| Sodium chloride | 2% by weight |

Method of Production

The fatty phase A (containing the fillers) and the aqueous phase B are weighed out separately and mixed with a spatula.

The aqueous phase is then introduced into the fatty phase, with an anchor stirrer, in a number of portions; stirring is maintained for approximately 10 minutes and then the emulsion is passed into a die-type homogenizer (ALM™, die A180). The observations and analyses of the emulsions are recorded in the following table:

| Powder x (% by weight) | Powder (t) | | Powder (3) | |
|---|---|---|---|---|
| | 2% | 5% | 2% | 5% |
| Viscosity (Brookfield LVT) spindle 4 speed 6 | 20 000 mPa·s | 8 500 mPa·s | 23 300 mPa·s | 9 260 mPa·s |
| Stability at 25° C. | Oily exudation at 3 months | Oily exudation at 3 months | Stable after 3 months | Stable after 3 months |
| Stability at 40° C. | Oily exudation at 1 month | Oily exudation at 3 months | Stable after 3 months | Stable after 3 months |
| Stability at 50° C. | Oily exudation at 1 month | Oily exudation at 3 months | Stable after 1 month | Stable after 3 months |
| Feel | Easy spreading Soft feel Light | Easy spreading Very soft feel | Easy spreading Soft feel Slight | Easy spreading Very soft feel |

| Powder x (% by weight) | Powder (t) | | Powder (3) | |
|---|---|---|---|---|
| | 2% | 5% | 2% | 5% |
| | powder effect | Remanent powder effect | powder effect | Remanent powder effect |

While preserving the sensorial properties of the initially selected powder, the compositions according to the invention allow significant improvement, without modification to the production process, of the stability of the emulsions produced, even for a low percentage of powder.

(4)—Enhancement of the Sensorial Properties of Compositions According to the Invention Relative to those of Conventional Powder Texturizers A number of compositions according to the invention were prepared from different powder texturizers, using the process described in paragraph (1) above.

The sensorial qualities of the powders, as raw materials, are evaluated by a panel of 15 experts, who record each evaluation criterion:

Quality of Feel Between Thumb and Index Finger (Criterion 1)

Scale: 0 to 5 (harsh feel: 0; very soft feel: 5);

Covering Power (Criterion 2)

Rating: from −1 to 1 (covering power identical to that of the control powder: 0; covering power greater than that of the control powder: 1; covering power inferior to that of the starting powder: −1);

Adhesion to the Skin (Criterion 3)

Rating: from 0 to 5 (no adhesion: 0; high adhesion: 5)

The properties of the following pairs of powders were compared:

Control powder ($t_a$): Micropearl™ M100

Inventive composition ($4_a$): Micropearl™ M100+Simulgel™ NS (weight ratio 80/20)

Control powder ($t_b$): Aerosil™ 200

Inventive composition ($4_b$): Aerosil™ 200+Simulgel™ NS: (weight ratio 80/20)

Control powder ($t_c$): Mica 1000™

Inventive composition ($4_c$): Mica 1000™+Simulgel™ NS (weight ratio 80/20)

Control powder ($t_d$): Dry Flo™

Inventive composition ($4_d$): Dry Flo™+Simulgel™ NS (weight ratio 80/20)

Control powder ($t_e$): titanium oxide USP

Inventive composition ($4_e$): titanium oxide USP+Simulgel™ NS (weight ratio 80/20)

Control powder ($t_f$): micronized zinc oxide: ZnO Neutral™

Inventive composition ($4_f$): neutral zinc oxide+Simulgel™ NS (weight ratio 80/20)

The results, recorded in the table below, are the arithmetic means of the scores for each of the three criteria.

|  | Compositions | | | | | | | | | | | |
|---|---|---|---|---|---|---|---|---|---|---|---|---|
|  | ($t_a$) | ($4_a$) | ($t_b$) | ($4_b$) | ($t_c$) | ($4_c$) | ($t_d$) | ($4_d$) | ($t_e$) | ($4_e$) | ($t_f$) | ($4_f$) |
| Criterion 1 | 3.5 | 4.7 | 1.2 | 2.5 | 3.0 | 4.1 | 3.2 | 4.3 | 0.5 | 1.5 | 0.7 | 1.4 |
| Criterion 2 | 0 | 0 | 0 | 0 | 0 | 1 | 0 | 0 | 0 | 0 | 0 | 0 |
| Criterion 3 | 2.5 | 4.4 | 1.9 | 2.8 | 3.3 | 4.1 | 2.2 | 3.6 | 3.7 | 4.9 | 4.0 | 4.7 |

Generally speaking, irrespective of the nature of the powder selected and its intrinsic properties, its initial, soft or harsh feel, its strong or weak natural adhesion to the skin, the compositions according to the invention score better for feel and skin adhesion than the control powders.

In the majority of cases the covering power of the compositions according to the invention is the same as that of the corresponding control powder.

The transparent powders such as polymethyl methacrylates (Micropearl), silicas or starch derivatives give transparent compositions, while the compositions produced from high-cover powders such as titanium oxide or zinc oxide have the same covering power of the original powder.

(5)—Evaluation of Sensorial Properties in Formulation

Pressed powders were prepared from the following formula:

| Pressed powder formula | |
|---|---|
| Formula | |
| Luzenac ™ 00C talc (composition according to the invention) | qs 100% 05.00% by weight |
| Mica 1000 ™ | 50.00% by weight |
| Colorant "FDC Yellow No. 6 Al lake" | 00.30% by weight |
| Colorant "Ariabel Sienna" | 00.20% by weight |
| Lanol ™ 1688 | 05.00% by weight |
| Dimethicone | 05.00% by weight |

The pulverulent compounds are mixed and then ground with a blade mixer. The hydrophobic binders are subsequently added in succession, with grinding of the mixture between each addition. The final mixture is ground again for several seconds. The powder is then compacted in a metal dish, using a Kemwall™ manual compactor, under a pressure of $80 \times 10^5$ Pa.

The sensorial qualities of the formulations are evaluated by a panel of 15 individuals, who record the following criteria on a scale from 0 to 5:

Ease of Removal with the Finger (Criterion 1)
Ratings from 0 to 5 (no removal: 0; very easy removal: 5)

Ease of Spreading on the Skin (Criterion 2)
Ratings from 0 to 5 (spreading difficult, with sticking: 0; very easy spreading: 5)

Release of the Colorant, Homogeneity of the Film, Distribution of the Colour (Criterion 3)
Ratings from 0 to 5 (heterogeneous film, poor coverage of the skin, poorly distributed colorant: 0; perfectly homogeneous film, uniform colour: 5)

Feel on the Skin (Criterion 4)
Ratings from 0 to 5 (harsh feel: 0; very soft feel: 5)

The properties of the following formulations were compared:

Formulation (t): Micropearl™ M310

Inventive formulation (5): Micropearl™ M100+Simulgel™ EG (weight ratio 60/40).

The results, recorded in the following table, are the arithmetic means of the scores for each of the four criteria.

| | Formulations | |
|---|---|---|
| | Formulation (t) | Formulation (5) |
| Visual appearance of the compact | Smooth and homogeneous appearance | Smooth and homogeneous appearance |
| Criterion 1 | 3.0 | 4.2 |
| Criterion 2 | 3.5 | 3.8 |
| Criterion 3 | 4.0 | 4.5 |
| Criterion 4 | 3.2 | 4.7 |

The compounds according to the invention are also notable texturizers in loose, pressed or cast powder formulas.

(6)—Stabilizing Effect within a Water-in-Silicone Emulsion

The properties of the series of emulsions prepared in paragraph (3) above were compared with those of the series of emulsions in silicone oils on the basis of the following formula:

| Phase A: | |
|---|---|
| DC5225C ™ | 20% by weight |
| DC345 ™ | 10% by weight |
| Sepicide ™ HB | 0.3% by weight |
| Micropearl ™ M310 | (0.8x)% by weight |
| Phase B | |
| Simulgel ™ EG | (0.2x)% by weight |
| Phase C | |
| Water | qs 100% |
| Sepicide ™ CI | 0.2% by weight |
| Glycerin | 5% by weight |
| Sodium chloride | 2% by weight |

Production Method

The fatty phase A (containing the fillers) and the aqueous phase B are weighed out separately and mixed using a spatula.

The aqueous phase C is introduced into the fatty phase with anchor stirring in a number of fractions; stirring is maintained for several minutes, Simulgel™ EG is introduced into the mixture, stirring is continued for approximately 10 minutes and then the emulsion is passed into a dye-type homogenizer (Alm™, dye A180). The observations and analyses of the emulsions are recorded in the following table:

|  | Prior art emulsions | | Inventive emulsions | |
| --- | --- | --- | --- | --- |
| x | 2 | 5 | 2 | 5 |
| Viscosity (Brookfield LVT) spindle 4 speed 6 | 21 000 mPa·s | 8 800 mPa·s | 23 300 mPa·s | 9 260 mPa·s |
| Stability at 25° C. | Oily exudation at 3 months | Stable after 3 months | Stable after 3 months | Stable after 3 months |
| Stability at 40° C. | Oily exudation at 3 months | Oily exudation at 3 months | Stable after 3 months | Stable after 3 months |
| Stability at 50° C. | Oily exudation at 1 month | Stable after 3 months | Stable after 1 month | Stable after 3 months |
| Feel | Easy spreading; soft feel; slight powder effect |  | Easy spreading soft feel slight powder effect | Easy spreading very soft feel remanent powder effect |

The use of the compositions according to the invention allows improvement in the temperature stability of silicone oil emulsions without detriment to their sensorial properties.

B) EXAMPLES OF COSMETIC FORMULATIONS

The compounds according to the invention are multi-functional texturizers which perform both in aqueous or oily liquid media and in moulded or powder solid formulations.

Example 1

Purifying Lotion for Greasy Skin

| | Formula | |
| --- | --- | --- |
| Phase A | Water | qs 100% |
| | Copper gluconate | 0.05% |
| | Zinc gluconate | 0.15% |
| Phase B | Micropearl ™ M310 + Simulgel ™ EG (75/25 by weight) | 3.50% |
| Phase C | Sepicide ™ HB | 0.30% |
| | Sepicide ™ LD | 0.80% |
| | Perfume | 0.10% |

Method

Phase A is prepared by dispersing the pulverulent compound in water with stirring and then phases B and C are added to the gel while continuing stirring.

Example 2

Powder Fluid for Impregnation on Towelettes

| | Formula | |
| --- | --- | --- |
| Phase A | Water | qs 100% |
| | Glycerin | 3.00% |
| | Micropearl ™ M310 + Simulgel ™ EG (60/40 by weight) (inventive composition) | 2.4% |
| Phase B | Sepicide ™ HB | 0.30% |
| | Sepicide ™ LD | 0.80% |
| | Perfume | 0.10% |

Method

Phase A is prepared by dispersing the pulverulent compound in water with stirring and then phases B and C are added to the gel while continuing stirring.

Example 3

Sprayable Softness Fluid

| | Formula | |
| --- | --- | --- |
| Phase A | Water | qs 100% |
| | Micropearl ™ M201 + Simulgel ™ EG (80/20 by weight) (inventive composition) | 5.00% |
| Phase B | DC345 ™ | 2.00% |
| Phase C | Sepicide ™ HB | 0.30% |
| | Sepicide ™ CI | 0.20% |
| | Perfume | 0.15% |
| | Sensiva ™ SC50 | 0.50% |

Method

Phase A is prepared by dispersing the inventive composition in water with stirring and then phases B and C are added to the gel while maintaining stirring.

Example 4

Freshening Aftersun Gel

| | Formula | |
| --- | --- | --- |
| Phase A | 90° alcohol | 20.00% |
| | Menthol | 00.05% |
| Phase B | Aqua/water | qs 100% |
| | Micropearl ™ M201 + Simulgel ™ EG (80/20 by weight) (inventive composition) | 10.00% |
| Phase C | Sepicalm ™ VG | 03.00% |
| | Perfume | 00.10% |
| | Colorant | qs |

Method

Phase A is prepared by dissolving menthol in ethanol.

Phase B is prepared by dispersing the inventive composition in water with stirring and then, when the gel is homogeneous, phase C and then phase A are added to phase B.

Example 5

Strengthening Body Treatment

| | Formula | |
|---|---|---|
| Phase A | Water | qs 100% |
| | Micropearl ™ 305 + Simulgel ™ EG (80/20 by weight) (inventive composition) | 8.50% |
| Phase B | Lanol ™ 99 | 5.00% |
| | Sepicalm ™ VG | 1.00% |
| | Sepilift ™ DPHP | 1.00% |
| Phase C | Sepicide ™ HB | 0.30% |
| | Sepicide ™ CI | 0.20% |
| | Perfume | 0.10% |

Method

The inventive composition is dispersed in water with stirring.

Phase B is prepared by heating the ester to 700° C. and then adding Sepicalm™ VG and Sepilift™ DPHP.

This phase B is added with stirring to phase A and then phase C is likewise added to the mixture thus formed.

Example 6

Invigorating Treatment

| | Formula | |
|---|---|---|
| Phase A | Water | qs 100% |
| | Glycerin | 02.50% |
| | Micropearl ™ 310 + Simulgel ™ EG (80/20 by weight) (inventive composition) | 15.00% |
| | Sepitonic ™ M3 | 01.00% |
| Phase B | Lanol ™ 99 | 05.00% |
| | DC345 ™ | 02.50% |
| Phase C | Perfume | 00.10% |
| | Sepicide ™ HB | 00.30% |
| | Sepicide ™ CI | 00.20% |

Method

Disperse the pulverulent compound with stirring in the aqueous phase and then introduce the fatty phase B into the aqueous phase A while continuing stirring. Add phase C to the final gel.

Example 7

Lipstick

| | Formula | |
|---|---|---|
| Phase A | Decyl oleate | 25.00% |
| | Titanium dioxide | 6.44% |
| | Yellow iron oxide | 3.04% |
| | Black iron oxide | 0.36% |
| | Colorant "DC Red 7" | 0.78% |
| | Colorant "FDC Yellow 6" | 0.70% |
| | Colorant "FDC Blue 1" | 0.17% |

| | -continued | |
|---|---|---|
| | Formula | |
| Phase B | Lanol ™ 99 | qs 100% |
| | Ozokerite | 11.75% |
| | Cetyl ricinoleate | 10.00% |
| | Octyldodecanol | 8.12% |
| | Beeswax | 4.20% |
| | Triisostearyl trilinoleate | 5.00% |
| | Cetyl palmitate | 4.50% |
| | Carnauba wax (Copernicia cerifera) | 2.28% |
| | Sepilift ™ DPHP | 1.00% |
| | Micropearl ™ MHB + Simulgel ™ NS (65/35 by weight) | 3.00% |
| Phase C | Perfume | 1.25% |
| | Tocopheryl acetate | 00.20% |

Method

Grind phase A in a bead mill.

Melt phase B at 85-90° C. and then add, with stirring, phase A, having ground it beforehand. Continue addition until dispersion is complete.

Introduce phase C with stirring. Cast the hot paste in moulds.

Example 8

Face Powder

| | Formula | |
|---|---|---|
| Phase A | Givobio ™ GCu | 0.50% |
| | Lipacide ™ C8G | 0.50% |
| | Lipacide UG | 0.50% |
| | Micropearl MHB ™ + Sepigel ™ 305 (60% + 40%) (inventive composition) | 5.00% |
| | Mica | 50.00% |
| | Talc | 33.00% |
| | Colorant "FDC Yellow 6 lake" | 0.30% |
| | Colorant "Ariabel Sienna" | 0.20% |
| Phase B | Lanol ™ 99 | 5.00% |
| Phase C | Dimethicone | 5.00% |

Method

Weigh out all the powders (phase A) and grind them dry in a cutter mill.

Add phase B and repeat the same grinding time as for phase A.

Add phase C and repeat the same grinding operation as for phase B.

The powder thus prepared is subsequently pressed into jars using a Kenwall™ manual compactor under a pressure of $80 \times 10^5$ Pa.

Example 9

Foundation

| | Formula | |
|---|---|---|
| Phase A | Water | 9.50% |
| | Butylene glycol | 2.00% |
| | PEG-400 | 2.00% |
| | Pecosil ™ PS100 | 0.50% |

-continued

| | Formula | |
|---|---|---|
| | Sodium hydroxide | qs pH = 9 |
| | Titanium dioxide | 3.50% |
| | Talc | 1.00% |
| | Yellow iron oxide | 0.41% |
| | Red iron oxide | 0.15% |
| | Black iron oxide | 0.025% |
| Phase B | Montanov ™ L | 2.00% |
| | Lanol ™ 99 | 4.00% |
| | Caprylic/capric triglyceride | 4.00% |
| Phase C | DC345 ™ | 2.00% |
| | Xanthan gum | 0.30% |
| | Aluminium magnesium silicate | 1.00% |
| Phase D | Water | qs 100% |
| | Tetrasodium EDTA | 0.05% |
| | Micropearl M305 ™ + Simulgel ™ NS (80%/20%) (inventive composition) | 2.00% |
| Phase E | Sepicide ™ HB | 0.50% |
| | Sepicide ™ CI | 0.30% |
| | Perfume | 0.20% |

Method

The liquid compounds of phase A are mixed and then the pH is adjusted before the pigments are added; this pigmentary phase is ground using a bead mill.

Phase B is subsequently melted at 75° C.

The water is also heated to 75° C. before the addition of phase D and then of phase A.

Thereafter phase C is added to phase B, and this mixture is introduced into the hot aqueous phase before the emulsifying device is started.

The emulsion is then gradually cooled and the constituents of phase E are added at 30° C.

Example 10

Coloured Cream Gel

| | Formula | |
|---|---|---|
| Phase A | Water | 10.00% |
| | Butylene glycol | 4.00% |
| | PEG-400 | 4.00% |
| | Pecosil ™ PS100 | 1.50% |
| | Sodium hydroxide | qs pH = 7 |
| | Titanium dioxide | 2.00% |
| | Yellow iron oxide | 0.80% |
| | Red iron oxide | 0.30% |
| | Black iron oxide | 0.05% |
| Phase B | Lanol ™ 99 | 4.00% |
| | Caprylic/capric triglyceride | 4.00% |
| | DC345 ™ | 4.00% |
| | Sepicide ™ HB | 0.30% |
| | Perfume | 0.20% |
| Phase C | Water | qs 100% |
| | Tetrasodium EDTA | 0.05% |
| | Sepicontrol ™ A5 | 4.00% |
| | Sepicide ™ CI (imidazolidinylurea - SEPPIC) | 0.20% |
| Phase D | Micropearl M100 ™ + Sepigel ™ 305 (80%/20%) (inventive composition) | 17.5% |

Method

The liquid compounds of phase A are mixed before the pigments are added and then this pigmentary phase A is ground using a bead mill.

Phase D is introduced into phase C with turbulent stirring. When the gel has formed and is homogeneous, the fatty phase B is added and then, finally, the pigment paste A.

Example 11

Water-Silicone Sun Emulsion

| | Formula | |
|---|---|---|
| Phase A | DC5225C ™ | 20.00% |
| | DC345 ™ | 10.00% |
| | Sepicalm ™ VG | 3.00% |
| | Titanium dioxide | 5.00% |
| | Zinc oxide Z-Cote ™ + Simulgel NS ™ (80%/20%) (inventive composition) | 5.00% |
| | Sepicide HB ™ | 0.30% |
| | Perfume | 0.05% |
| Phase B | Water | qs 100% |
| | Sepicide ™ CI | 0.20% |
| | Glycerin | 5.00% |
| | Sodium chloride | 2.00% |

Method

Phase A is prepared by mixing the silicones and Sepicalm™ VG and then dispersing the inorganic fillers with gentle stirring until their wetting is complete, then by adding the preservative and the perfume.

The aqueous phase B is prepared separately and then introduced slowly into phase A with moderate stirring. The step of homogenization commences after all of the ingredients have been introduced.

In a continuous aqueous medium the compounds of the invention are particularly effective in performance terms, since in addition to their sensorial qualities they exhibit suspension properties and an intrinsic viscosity-increasing effect which can be modified as a function of the amount in which they are used. Simple aqueous dispersion of the compounds of the invention, without addition of any other ingredient, results in a stable powder suspension whose viscosity can be modified in accordance with the amount of powder introduced.

This suspension is also able to stabilize, in accordance with the amount of powder, oils of any kind and solvents which are commonly used in cosmetology, such as ethanol and glycols such as propylene glycol, butylene glycol or hexylene glycol.

In a continuous oily liquid medium, a significant stabilizing effect is also provided by the compounds of the invention, in accordance with the nature of the powder selected.

The compounds of the invention are effective texturizers in all types of formulation, providing:

a very soft feel, improved relative to that of powder texturizers used alone;

excellent adhesion to the skin, greater than that of powder texturizers used alone.

The characteristics of the commercial products used in the examples above are as follows:

Micropearl™ M305: silky, water-dispersible powder based on crosslinked polymethyl methacrylate Micropearl™ M310: silky, hydrophobic powder based on crosslinked polymethyl methacrylate Micropearl™ M100: silky, water-dispersible powder based on polymethyl methacrylate Micropearl™ M201: silky, water-dispersible powder based on crosslinked polymethyl methacrylate with a particle size of approximately 1 to 5 μm Micropearl™ MHB: silky, hydrophobic powder based on crosslinked polymethyl methacrylate;

Simulgel™ EG: self-invertible inverse copolymer latex like those described in international publication WO 99/36445 (INCI name: Hydroxyethyl acrylate/Sodium acryloyldimethyl taurate copolymer and Isohexadecane and Polysorbate 80), sold by SEPPIC;

Simulgel™ NS: self-invertible inverse copolymer latex like those described in international publication WO 99/36445 (INCI name: Hydroxyethyl acrylate/Sodium acryloyldimethyl taurate copolymer and squalane and Polysorbate 60), sold by SEPPIC;

Sepigel™305: self-invertible inverse latex (INCI name: Polyacrylamide/C13-14 Isoparaffin/Laureth-7)

DC5225C™: mixture of cyclopentasiloxane and dimethicone copolyol, sold by Dow Corning;

DC345™: cyclomethicone sold by Dow Corning;

Dry Flo™: starch modified with aluminium and octenyl succinate, sold by National Starch;

Mica 1000™: mica powder sold by Sciama;

Aerosil™ 200: silica sold by Degussa;

ZnO Neutral™: micronized zinc oxide, sold by Harmann & Reimer;

Sepicide™ CI: imidazolinylurea (preservative), sold by SEPPIC;

Sepicide™ HB: mixture of phenoxyethanol, methylparaben, ethylparaben, propylparaben and butylparaben (preservative), sold by SEPPIC;

Sepicide™ LD: phenoxyethanol, sold by SEPPIC;

Sensiva™ SC50: 1-(2-ethylhexyl)glycerol, sold by Schuelke & Mayr;

Sepicalm™ VG: composition like those described in international publication WO 99/45899 (INCI name: sodium palmitoyl proline and waterlily flower extract), sold by SEPPIC;

Sepilift™ DPHP: (INCI name: Dipalmitoyl hydroxy-proline), sold by SEPPIC;

Sepitonic™ M3: mixture of magnesium aspartate, copper gluconate and zinc gluconate sold by SEPPIC;

Givobio™ GCu: copper gluconate sold by SEPPIC;

Lipacide™ UG: undecylenoylglycine sold by SEPPIC;

Lipacide™ C8G: octanoylglycine sold by SEPPIC;

Lanol™ 99 isononyl isononanoate sold by SEPPIC;

Lanol™ 1688: cetearyl ethylhexanoate sold by SEPPIC;

Pecosil™ PS100 is the dimethicone copolyol phosphate sold by Phoenix;

Montanov™ L: emulsifier based on C14-C22 alcohol and C12-C20 alkyl polyglucoside, like those described in European patent application EP 0 995 487;

Sepicontrol™ A5: mixture of capryloylglycine, sarcosine and extract of Cinnamonum zylanicum, sold by SEPPIC, like those described in international publication WO 99/00109.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

The invention claimed is:

1. A texturizing composition, consisting essentially of:
   a) from about 1% to about 90% of at least one self-invertible inverse latex by weight; and
   b) from about 10% to about 99% of at least one powder by weight, wherein, said self-invertible inverse latex comprises an oil phase, an aqueous phase, at least one water-in-oil (W/O) emulsifier, at least one oil-in-water (O/W) emulsifier, and a branched or crosslinked polyelectrolyte, said polyelectrolyte is selected from the group consisting of:
   a homopolymer based on a monomer possessing either a strong acid function which is partly or totally in salt form or a weak acid function which is partly or totally in salt form,
   a copolymer based on at least one monomer possessing a strong acid function copolymerized either with at least one monomer possessing a weak acid function or with at least one neutral monomer, and
   a copolymer based on at least one monomer possessing a weak acid function copolymerized with at least one neutral monomer or with a monomer possessing a weak acid function.

2. The composition according to claim 1, wherein said composition consists essentially of:
   a) from about 5% to about 80% of said self-invertible inverse latex; and
   b) from about 20% to about 95% of said powder.

3. The composition according to claim 2, wherein said composition is essentially free of fillers.

4. The composition according to claim 1, wherein said composition is in powder form.

5. The composition according to claim 1, wherein said self-invertible latex is in liquid form.

6. The composition according to claim 1, wherein said oil phase is in the range of from about 15% to about 40% by weight of the total latex.

7. The composition according to claim 6, wherein said oil phase is in the range of from about 20% to about 25%.

8. The composition according to claim 1, wherein said oil phase comprises saturated hydrocarbons.

9. The composition according to claim 1, wherein said oil-in-water (O/W) emulsifier and said water-in-oil (W/O) emulsifier, together, are from about 2.5% to about 15% by weight of the total latex.

10. The composition according to claim 9, wherein said emulsifiers are from about 4% to about 9%.

11. The composition according to claim 1, wherein said polyelectrolyte is in the range of from about 20% to about 70% by weight of the total latex.

12. The composition according to claim 11, wherein said polyelectrolyte is in the range of from about 25% to about 50%.

13. The composition according to claim 1, wherein said polyelectrolyte is selected from the group consisting of:
   a) copolymer of acrylic acid partly in sodium salt form and acrylamide, cross linked with methylenebis (acrylamide);
   b) copolymer of 2-methyl-2-[(1-oxo-2-propenyl)amino]-1-propanesulphonic acid partly in sodium salt form and acrylamide, cross-linked with methylenebis (acrylamide);
   c) copolymer of 2-methyl-2-[(1-oxo-2-propenyl)amino]-1-propanesulphonic acid partly in sodium salt form and acrylic acid partly in sodium salt form, cross-linked with methylenebis (acrylamide);
   d) copolymer of 2-methyl-2-[(1-oxo-2-propenyl)amiflo]-1-propanesuiphonic acid partly in sodium salt form and 2-hydroxyethyl acrylate, cross-linked with methylenebis (acrylamide);

e) homopolymer of 2-methyl-2-[(1-oxo-2-propenyl)amino]-1-propanesulphonic acid partly in sodium salt form, cross-linked with methylenebis (acrylamide);

f) homopolymer of acrylic acid partly in arnmonium salt or monoethanolamine salt form, cross-linked with sodium diallyloxyacetate; and g) homopolymer of acrylic acid partly in ammonium or monoethanolamine salt form, cross-linked with triallylamine.

14. The composition according to claim 1, wherein said powder is in spherical form.

15. The composition according to claim 1, wherein said powder is homogenous.

16. The composition according to claim 1, wherein said powder comprises at least one component selected from the group consisting of:

a) synthetic materials;
b) natural materials;
c) organic materials;
d) inorganic materials;
e) hydrophilic materials; and
f) hydrophobic materials.

17. The composition according to claim 7, wherein said powder contains a mean diameter in the range of from about 0.01 µm to about 250 µm.

18. The composition according to claim 17, wherein said diameter is in the range of from about 1 µm to about 50 µm.

19. The composition according to claim 1, wherein said powder comprises porous polylmethyl methacrylate microspheres.

20. The composition according to claim 19, wherein said porous polymethyl methacrylate microsphere has a specific surface area greater than or equal to $0.5 \ m^2$ per gram.

21. The composition according to claim 2, wherein said powder is at least about 50% by weight of the total composition.

* * * * *